United States Patent [19]

Smith

[11] 4,125,734

[45] Nov. 14, 1978

[54] 5-OXA-13,14-DIDEHYDRO-11-DEOXY-PGE$_1$ COMPOUNDS

[75] Inventor: Herman W. Smith, Kalamazoo, Mich.

[73] Assignee: The Upjohn Company, Kalamazoo, Mich.

[21] Appl. No.: 820,970

[22] Filed: Aug. 1, 1977

Related U.S. Application Data

[62] Division of Ser. No. 657,740, Feb. 13, 1976.

[51] Int. Cl.$^2$ .................................. G07C 17/00
[52] U.S. Cl. .................................. 560/121; 562/503
[58] Field of Search .................. 260/514 D; 560/121

[56] References Cited

PUBLICATIONS

Fried et al., Proc. Nat. Acad. Sci. 70, 1579 (1973).

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is replaced by a triple bond. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

67 Claims, No Drawings

5-OXA-13,14-DIDEHYDRO-11-DEOXY-PGE$_1$ COMPOUNDS

The present application is a divisional application of Ser. No. 657,740, filed Feb. 13, 1976, now pending issuance as a U.S. patent.

The present invention relates to prostaglandin analogs, for which the essential material constituting disclosure therefor is incorporated by reference here from Ser. No. 820,974, filed Aug. 1, 1977, now U.S. Pat. No. 4,099,015, issued July 4, 1978, which is a divisional application of Ser. No. 657,740.

I claim:
1. A prostaglandin analog of the formula

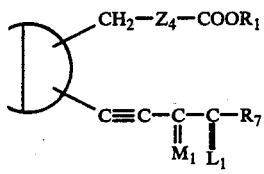

wherein D is

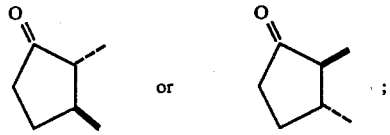

wherein $Z_4$ is

—CH$_2$—O—CH$_2$—(CH$_2$)$_g$—CH$_2$—,

—(CH$_2$)$_2$—O—(CH$_2$)$_g$—CH$_2$—, or

—(CH$_2$)$_3$—O—(CH$_2$)$_g$—;

wherein $g$ is one, 2, or 3;
wherein $R_7$ is

—(CH$_2$)$_m$—CH$_3$, wherein $m$ is one to 5, inclusive;
wherein $L_1$ is

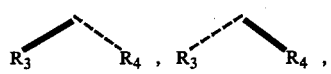

or a mixture of

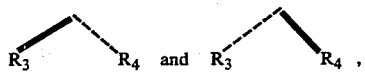

wherein $R_3$ and $R_4$ are hydrogen, methyl, or fluoro, being the same or different, with the proviso that one of $R_3$ and $R_4$ is methyl only when the other is hydrogen or methyl;
wherein $M_1$ is

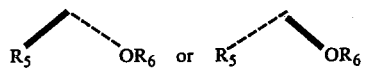

wherein $R_5$ and $R_6$ are hydrogen or methyl, with the proviso that one of $R_5$ and $R_6$ is methyl only when the other is hydrogen; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein D is

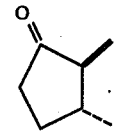

3. A compound according to claim 2, wherein $M_1$ is

4. A compound according to claim 3, wherein $g$ is one.

5. A compound according to claim 4, wherein $R_3$, $R_4$, $R_5$, and $R_6$ are all hydrogen.

6. 15-epi-5-Oxa-13,14-didehydro-8β,12α-11-deoxy-PGE$_1$, methyl ester, a compound according to claim 4.

7. A compound according to claim 2, wherein $M_1$ is

8. A compound according to claim 7, wherein $g$ is three.

9. A compound according to claim 7, wherein $g$ is one.

10. A compound according to claim 9, wherein $R_3$ and $R_4$ are both hydrogen.

11. A compound according to claim 10, wherein $R_6$ is methyl.

12. 5-Oxa-13,14-didehydro-8β,12α-11-deoxy-PGE$_1$, 15-methyl ether, a compound according to claim 11.

13. 5-Oxa-13,14-didehydro-8β,12α-11-deoxy-PGE$_1$, methyl ester, 15-methyl ether, a compound according to claim 11.

14. A compound according to claim 10, wherein $R_5$ and $R_6$ are both hydrogen.

15. 5-Oxa-13,14-didehydro-8β,12α-11-deoxy-PGE$_1$, a compound according to claim 14.

16. 5-Oxa-13,14-didehydro-8β,12α-11-deoxy-PGE$_1$, methyl ester, a compound according to claim 14.

17. A compound according to claim 9, wherein at least one of $R_3$ and $R_4$ is methyl.

18. A compound according to claim 17, wherein $R_3$ and $R_4$ are both methyl.

19. A compound according to claim 18, wherein $R_5$ is methyl.

20. 5-Oxa-15,16,16-trimethyl-13,14-didehydro-8β,12α-11-deoxy-PGE$_1$, methyl ester, a compound according to claim 19.

21. A compound according to claim 18, wherein $R_6$ is methyl.

22. 5-Oxa-16,16-dimethyl-13,14-didehydro-8β,12α-11-deoxy-PGE$_1$, methyl ester, 15-methyl ether, a compound according to claim 21.

23. A compound according to claim 18, wherein $R_5$ and $R_6$ are both hydrogen.

24. 5-Oxa-16,16-dimethyl-13,14-didehydro-8β,12α-11-deoxy-PGE$_1$, a compound according to claim 23.

25. 5-Oxa-16,16-dimethyl-13,14-didehydro-8β,12α-11-deoxy-PGE$_1$, methyl ester, a compound according to claim 23.

26. A compound according to claim 9, wherein at least one of $R_3$ and $R_4$ is fluoro.

27. A compound according to claim 26, wherein $R_3$ and $R_4$ are both fluoro.

28. A compound according to claim 27, wherein $R_5$ is methyl.

29. 5-Oxa-15-methyl-16,16-difluoro-13,14-didehydro-8β,12α-11-deoxy-PGE$_1$, methyl ester, a compound according to claim 28.

30. A compound according to claim 27, wherein $R_6$ is methyl.

31. 5-Oxa-16,16-difluoro-13,14-didehydro-8β,12α-11-deoxy-PGE$_1$, methyl ester, 15-methyl ether, a compound according to claim 30.

32. A compound according to claim 27, wherein $R_5$ and $R_6$ are both hydrogen.

33. 5-Oxa-16,16-difluoro-13,14-didehydro-8β,12α-11-deoxy-PGE$_1$, a compound according to claim 32.

34. 5-Oxa-16,16-difluoro-13,14-didehydro-8β,12α-11-deoxy-PGE$_1$, methyl ester, a compound according to claim 32.

35. A compound according to claim 1, wherein D is

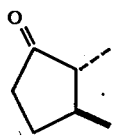

36. A compound according to claim 35, wherein $M_1$ is

37. A compound according to claim 36, wherein g is one.

38. A compound according to claim 37, wherein $R_3$, $R_4$, $R_5$, and $R_6$ are all hydrogen.

39. 15-epi-5-Oxa-13,14-didehydro-11-deoxy-PGE$_1$, methyl ester, a compound according to claim 38.

40. A compound according to claim 35, wherein $M_1$ is

41. A compound according to claim 40, wherein g is three.

42. A compound according to claim 40, wherein g is one.

43. A compound according to claim 42, wherein $R_3$ and $R_4$ are both hydrogen.

44. A compound according to claim 43, wherein $R_6$ is methyl.

45. 5-Oxa-13,14-didehydro-11-deoxy-PGE$_1$, 15-methyl ether, a compound according to claim 44.

46. 5-Oxa-13,14-didehydro-11-deoxy-PGE$_1$, methyl ester, 15-methyl ether, a compound according to claim 44.

47. A compound according to claim 43, wherein $R_5$ and $R_6$ are both hydrogen.

48. 5-Oxa-13,14-didehydro-11-deoxy-PGE$_1$, a compound according to claim 47.

49. 5-Oxa-13,14-didehydro-11-deoxy-PGE$_1$, methyl ester, a compound according to claim 47.

50. A compound according to claim 42, wherein at least one of $R_3$ and $R_4$ is methyl.

51. A compound according to claim 50, wherein $R_3$ and $R_4$ are both methyl.

52. A compound according to claim 51, wherein $R_5$ is methyl.

53. 5-Oxa-15,16,16-trimethyl-13,14-didehydro-11-deoxy-PGE$_1$, methyl ester, a compound according to claim 52.

54. A compound according to claim 51, wherein $R_6$ is methyl.

55. 5-Oxa-16,16-dimethyl-13,14-didehydro-11-deoxy-PGE$_1$, methyl ester, 15-methyl ether, a compound according to claim 54.

56. A compound according to claim 51, wherein $R_5$ and $R_6$ are both hydrogen.

57. 5-Oxa-16,16-dimethyl-13,14-didehydro-11-deoxy-PGE$_1$, a compound according to claim 56.

58. 5-Oxa-16,16-dimethyl-13,14-didehydro-11-deoxy-PGE$_1$, methyl ester, a compound according to claim 56.

59. A compound according to claim 42, wherein at least one of $R_3$ and $R_4$ is fluoro.

60. A compound according to claim 59, wherein $R_3$ and $R_4$ are both fluoro.

61. A compound according to claim 60, wherein $R_5$ is methyl.

62. 5-Oxa-15-methyl-16,16-difluoro-13,14-didehydro-PGE$_1$ 11-deoxy-PGE$_1$, methyl ester, a compound according to claim 61.

63. A compound according to claim 60, wherein $R_6$ is methyl.

64. 5-Oxa-16,16-difluoro-13,14-didehydro-11-deoxy-PGE$_1$, methyl ester, 15-methyl ether, a compound according to claim 63.

65. A compound according to claim 60, wherein $R_5$ and $R_6$ are both hydrogen.

66. 5-Oxa-16,16-difluoro-13,14-didehydro-11-deoxy-PGE$_1$, a compound according to claim 65.

67. 5-Oxa-16,16-difluoro-13,14-didehydro-11-deoxy-PGE$_1$, methyl ester, a compound according to claim 65.

* * * * *

UNITED STATES PATENT OFFICE
CERTIFICATE OF CORRECTION

Patent No. 4,125,734     Dated November 14, 1978

Inventor(s) Herman W. Smith

It is certified that error appears in the above-identified patent and that said Letters Patent are hereby corrected as shown below:

Column 2, lines 55-59, cancel the lines (Claims 19 and 20);

Column 4, lines 22-26, cancel the lines (Claims 52 and 53).

On the cover sheet "67 Claims" should read
-- 63 Claims --.

Signed and Sealed this

Tenth Day of April 1979

[SEAL]

Attest:

RUTH C. MASON
*Attesting Officer*

DONALD W. BANNER
*Commissioner of Patents and Trademarks*